United States Patent [19]
Stewart et al.

[11] Patent Number: 5,627,646
[45] Date of Patent: May 6, 1997

[54] METHOD FOR LOCATING FLAWS IN A SMOOTH SURFACE OF AN OBJECT

[75] Inventors: Paul J. Stewart; Yifan Chen, both of Ann Arbor, Mich.

[73] Assignee: Ford Motor Company, Dearborn, Mich.

[21] Appl. No.: 505,426

[22] Filed: Jul. 21, 1995

[51] Int. Cl.$^6$ ............................................. G01B 11/30
[52] U.S. Cl. ................................. 356/371; 356/237
[58] Field of Search ............................ 356/371, 237, 356/446, 124.5, 445, 448, 376, 429–431; 364/525, 551.01, 552

[56] References Cited

U.S. PATENT DOCUMENTS

| | | | |
|---|---|---|---|
| 4,209,252 | 6/1980 | Arditty et al. | 356/4 |
| 4,629,319 | 12/1986 | Clarke et al. | 356/237 |
| 4,641,972 | 2/1987 | Halioua et al. | 356/376 |
| 4,792,232 | 12/1988 | Jobe et al. | 356/394 |
| 4,846,578 | 7/1989 | Morita et al. | 356/124.5 |
| 5,092,676 | 3/1992 | Harata et al. | 356/124.5 |
| 5,141,320 | 8/1992 | Harata et al. | 356/124.5 |
| 5,142,648 | 8/1992 | Fitts et al. | 356/446 |
| 5,155,558 | 10/1992 | Tannenbaum et al. | 356/124.5 |
| 5,160,977 | 11/1992 | Utsumi | 356/376 |
| 5,175,601 | 12/1992 | Fitts | 356/376 |
| 5,237,404 | 8/1993 | Tanaka et al. | 356/376 |
| 5,243,665 | 9/1993 | Maney et al. | 382/8 |
| 5,289,264 | 2/1994 | Steinbichler | 356/376 |

OTHER PUBLICATIONS

Computer–Aided Design, Butterworth–Heinemann, vol. 26, No. 4, Apr. 1994.
Designing Fair Curves and Surfaces:shape quality in geometric modeling and computer–aided design, edited by Nickolas S. Sapidis, 1994.
Highlight lines for surface quality control and shape manipulation, Yifan Chen, 1993.

*Primary Examiner*—Hoa Q. Pham
*Attorney, Agent, or Firm*—David B. Kelley, Esq.; Roger L. May, Esq.

[57] ABSTRACT

A method for locating flaws in a smooth surface using at least one light source includes the steps of setting the light source at a predetermined length above the smooth surface, locating a highlight line, translating the light source across the smooth surface to create a plurality of highlight lines and locating distortions in the smooth surface.

7 Claims, 4 Drawing Sheets

METHOD FOR LOCATING FLAWS IN A SMOOTH SURFACE OF AN OBJECT

BACKGROUND OF THE INVENTION

1. Field of the Invention

The present invention relates generally to smooth surfaces formed on an object and, more particularly, to a method for locating flaws in a smooth surface formed on an object.

2. Description of the Related Art

Current methods for creating a smooth surfaced object are man-hour intensive. It requires computer aided designs (CAD) resulting in the preparation of a finished surface which is viewed by the individual under special lighting conditions. Aberrations in the reflected light indicate a distortion in the finished surface which will detract from appearance and aesthetics of the surface. This iterative process of creating surfaces which are subsequently redone due to distortions detected by the human eye is costly and time consuming.

SUMMARY OF THE INVENTION

Accordingly, the present invention is a method used for locating flaws in a smooth surface of an object using at least one light source. The method includes the steps of setting the light source a predetermined length above the smooth surface and locating a highlight line. The method also includes translating the light source across the smooth surface to create a plurality of highlight lines and locating flaws in the smooth surface.

One advantage of the present invention is that the method reduces the man-hours associated with creating a smooth surface. A second advantage of the present invention is the reduction of iterative creations of the smooth surface reducing the time and costs associated with the creation of these smooth surfaces.

Other features and advantages of the present invention will be readily appreciated as the same becomes better understood by reference to the subsequent description when considered in connection with the accompanying drawings.

DESCRIPTION OF THE PREFERRED EMBODIMENT(S)

Figure 1:
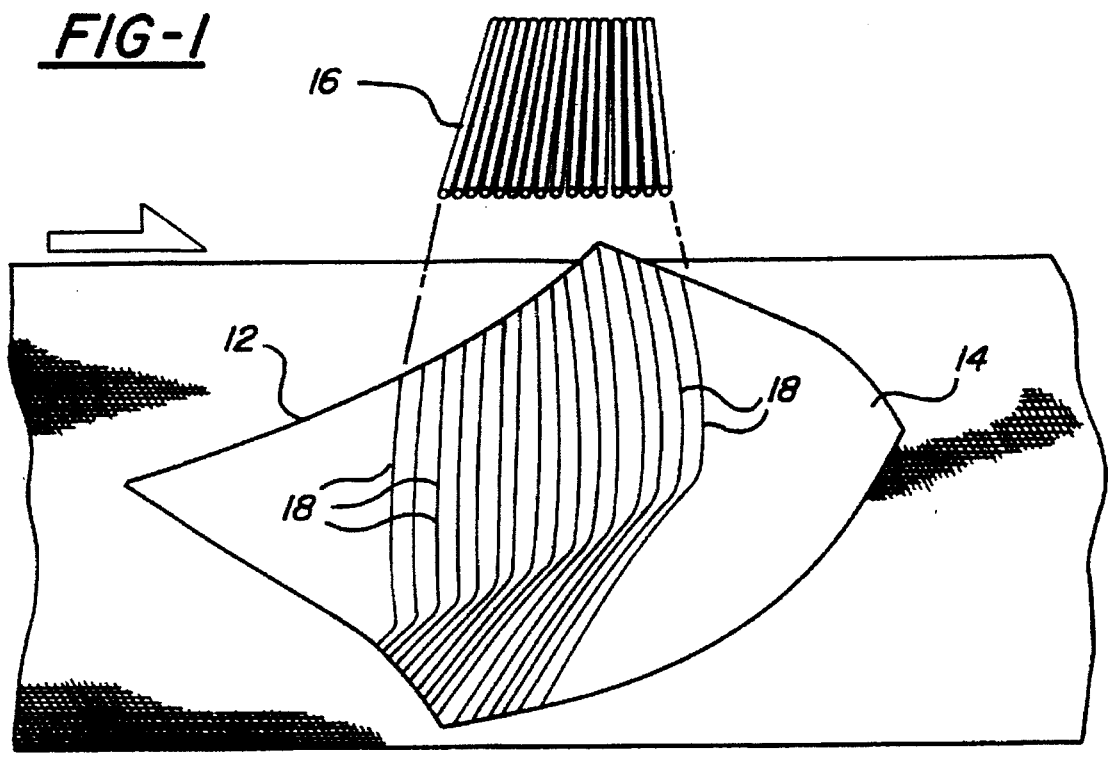
FIG. 1 is a perspective view of a first surface having a plurality of highlight lines created by a plurality of light sources shining down on the first surface.
Figure 2:
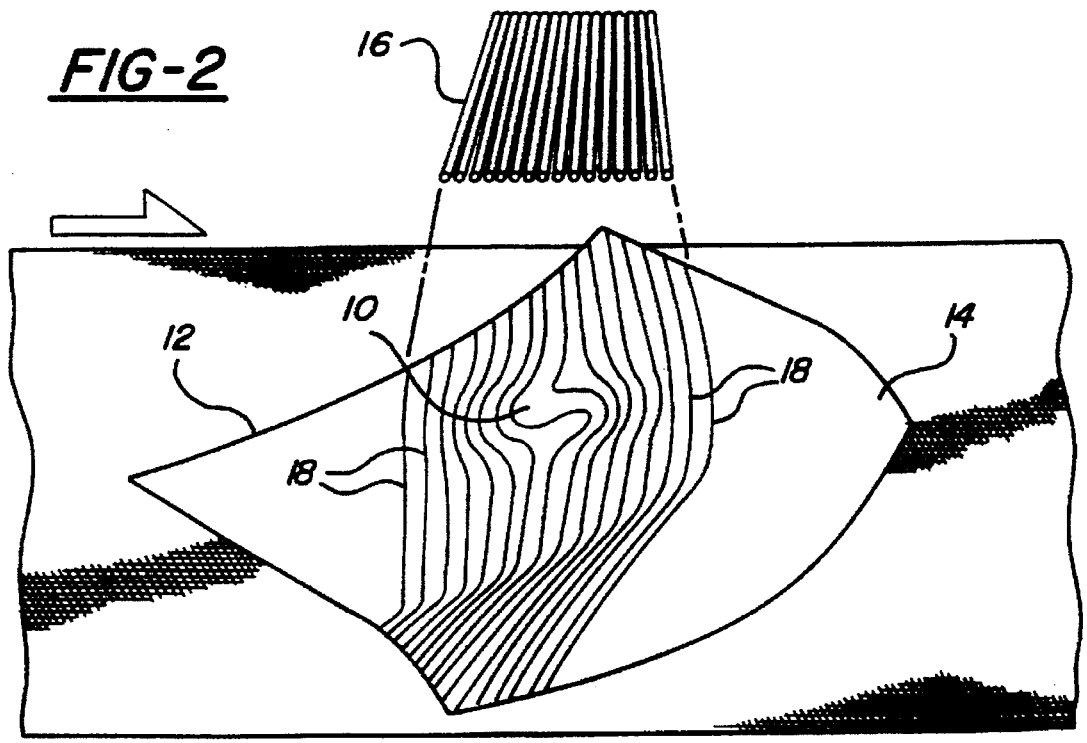
FIG. 2 is a perspective view of a second surface having a distortion accentuated by the highlight lines created by the plurality of light sources shining down on the second surface.

Referring to FIGS. 1 and 2, one embodiment of a method, according to the present invention, described herein is used for locating flaws 10 in a smooth surface 12 of an object and to determine the severity of those flaws 10. The flaws or distortions 10 detract from the aesthetic appearance on the smooth surface 12. These flaws 10 differ from a designed bend 14 in the smooth surface 12 in that the flaws 10 serve no useful function and detract from the quality, perceived or real, of the preferred design of the smooth surface 12. The flaws 10 are subjectively perceived by individuals from which a consensus as to the severity thereof is difficult to achieve. The flaws 10 are, therefore, objectively tested removing the subjectiveness of the method. The flaws 10 are objectively defined below. In one embodiment, the smooth surface 12 is on an object such as a part or panel of a motor vehicle (not shown).

At least one light source 16 is set at a height above the smooth surface 12 such that light emitted from the light source 16 shines down on the smooth surface 12 and reflects out and away from the smooth surface 12. In one embodiment, a plurality of light sources 16 are used, as may be seen in FIGS. 1 and 2. In another embodiment, the light source 16 may be generated by a computer.

A highlight line 18 is located on the smooth surface 12. A highlight line 18 is defined as the line in which light is emitted from the light source 16 which is reflected off the smooth surface 12 directly at the point of emission along the light source 16. Because the light source 16 extends through a finite portion of space in a linear fashion, similar to a standard fluorescent bulb, light is emitted down toward the smooth surface 12 along the length of the light source 16. Therefore, at each point along the length of the light source 16, a beam of light is sent down toward the smooth surface 12 where it is reflected back to the light source 16 along the same path in which it traveled to the smooth surface 12. It is these light beams that are reflected along the same path in which are transmitted that define the highlight lines 18. In one embodiment, because the light sources 16 are parallel to each other and spaced equidistantly therefrom, the highlight lines 18 are parallel to each other when a surface is smooth.

However, as in FIG. 2, a flaw 10 may be discovered when the highlight lines 18 are no longer parallel to each other. This analysis works as long as the smooth surface 12 is also planar. More specifically, additional analysis is required when the smooth surface 12 includes a bend 14 such that the highlight lines 18 are bent along the bend 14 of the smooth surface 12.

The light source 16 is translated across the smooth surface 12 to create a plurality of highlight lines 18. Alternatively, a plurality of highlight lines 18 may be produced by a using a plurality of light sources 16 spaced equidistantly and parallel across the entire smooth surface 12. Once the highlight lines 18 extend across the smooth surface 12, the flaws 10 are then located.

Figure 6A:
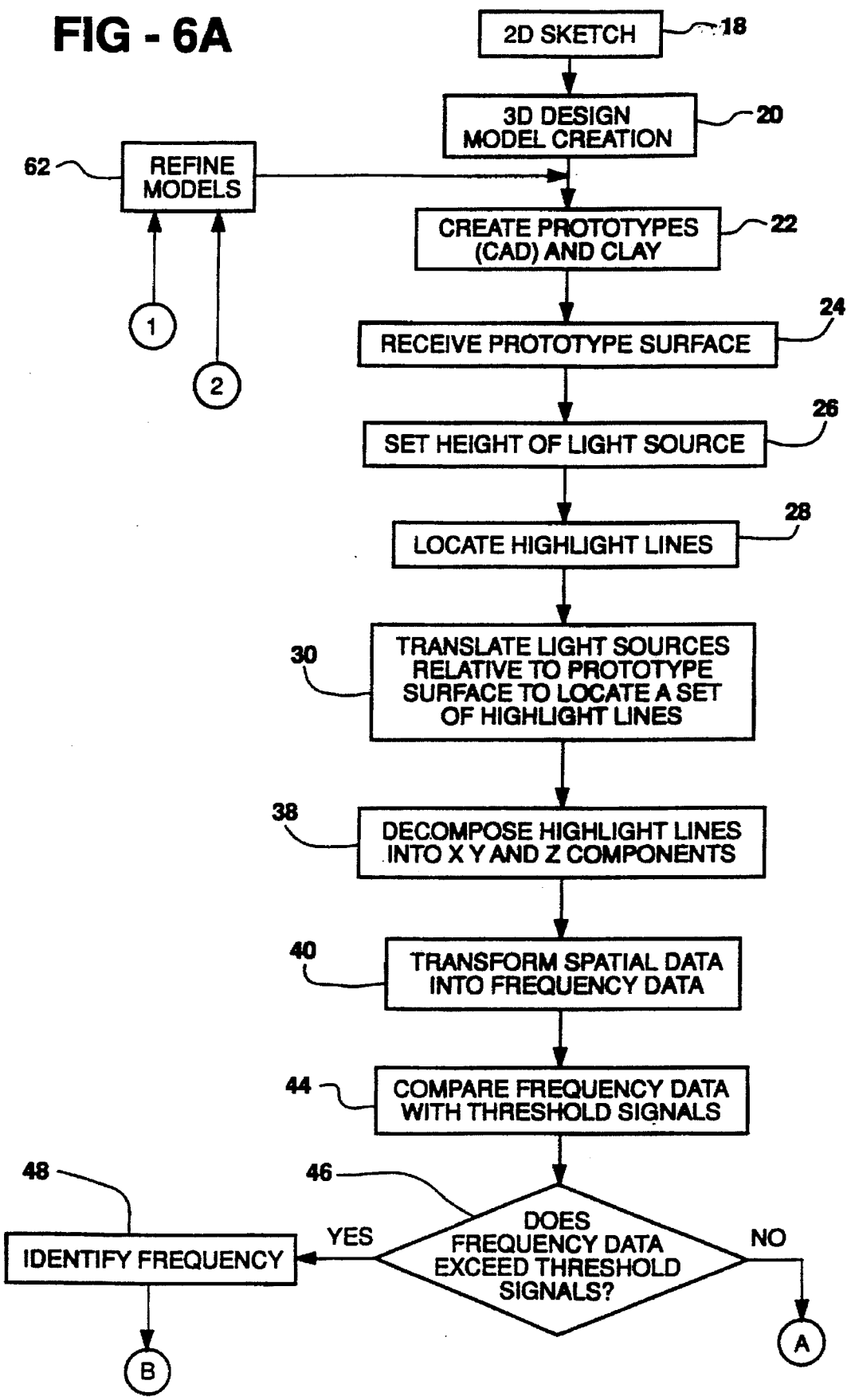
FIGS. 6A and 6B are a flowchart of a method of locating flaws in a smooth surface of an object according to the present invention.
Figure 6B:
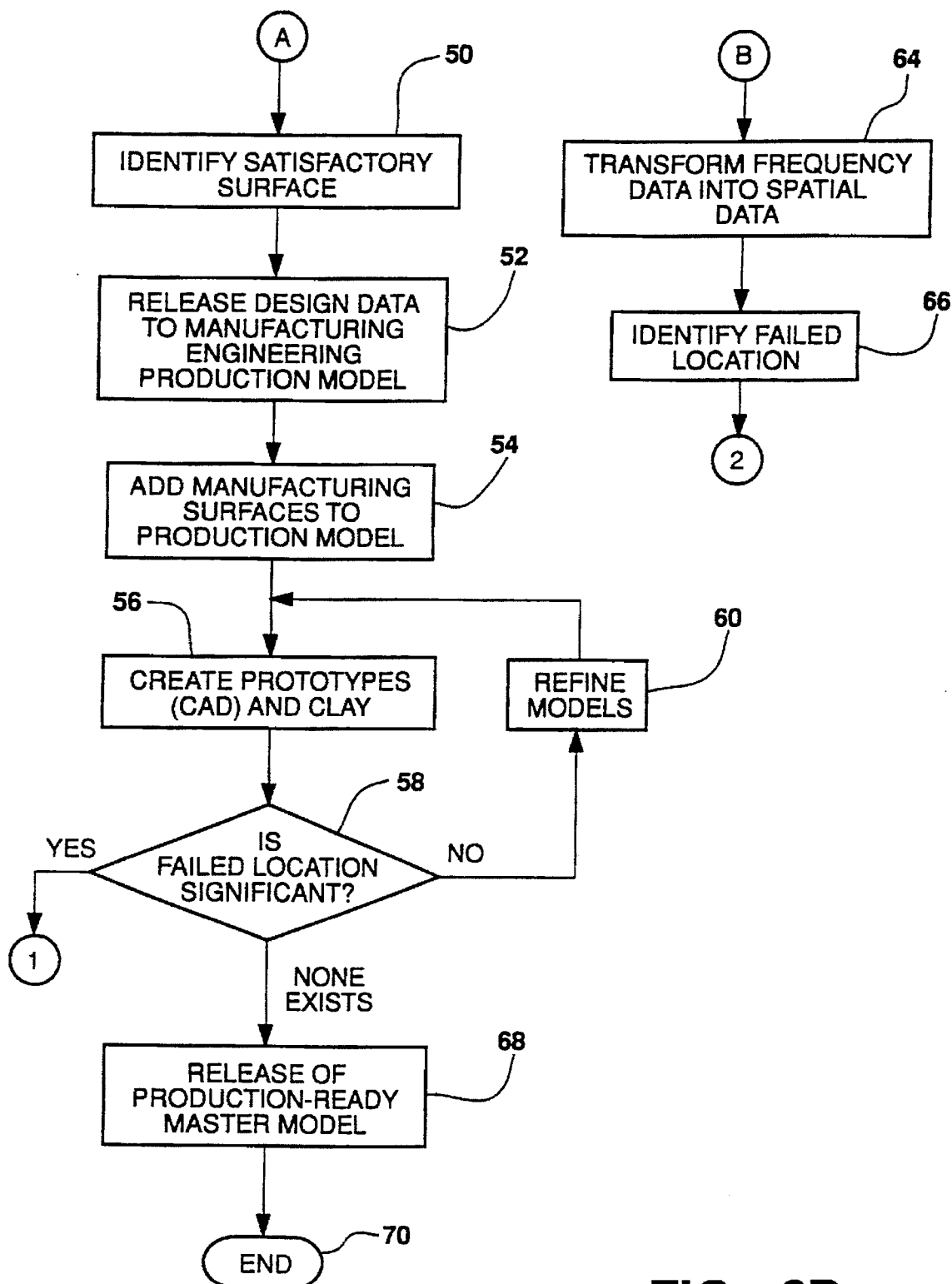

Referring to FIGS. 6A and 6B, one embodiment of a method for locating flaws 10 in a smooth surface 12, according to the present invention, is shown graphically in flowchart form. In the first step at 18, a two dimensional sketch of a desired surface is generated. From this two dimensional sketch, a three dimensional model is created at 20. The model is used to create a three dimensional prototype at 22. The three dimensional prototype may be created from a computer aided design (CAD) system or from a clay model, depending on the technique desired for the particular application.

Once the prototype is created, the analysis of the prototype surface is begun at 24. First, the height of the light source 16 is set at 26. In one embodiment, the height of the light source 16 is defined at a particular height. In a second embodiment, the height of the light source 16 is dependent upon how arcuate or, alternatively, how planar of the smooth surface 12.

With the light source 16 set at a defined height, a highlight line 18 is located at 28. A highlight line 18 is a line consisting of a plurality of points wherein the points are defined by rays of light (not shown) which are emitted from the light source 16 and reflected off the smooth surface 12 in the exact direction from which the rays of light impinged on the smooth surface 12. Said another way, the points defining a highlight line 18 are those created by rays of light which are reflected off the smooth surface 12 in a direction equal and opposite to the direction at which the rays of light are transmitted, i.e., the same path.

After the highlight line 18 is located, the light source 16 is translated relative to the prototype surface to locate or define a plurality of highlight lines 18 at 30. The light source 16 does not change its absolute height and, therefore, the relative distance between the light source 16 and the smooth surface 12 may vary depending on the shape of the smooth surface 12. Alternatively, and as shown in FIGS. 1 and 2, a plurality of light sources 16 may be used which minimize or even eliminate the need for the translation step 30.

Figure 3:
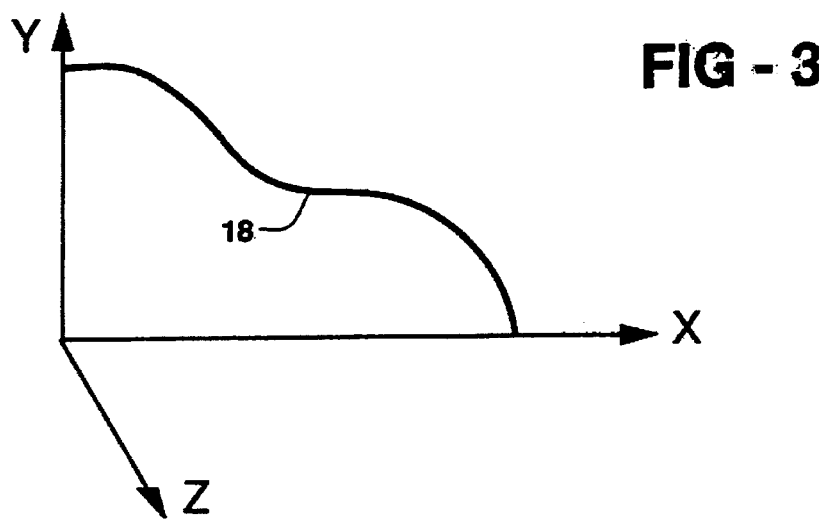
FIG. 3 is a graphic representation of a single highlight line.
Figure 4:
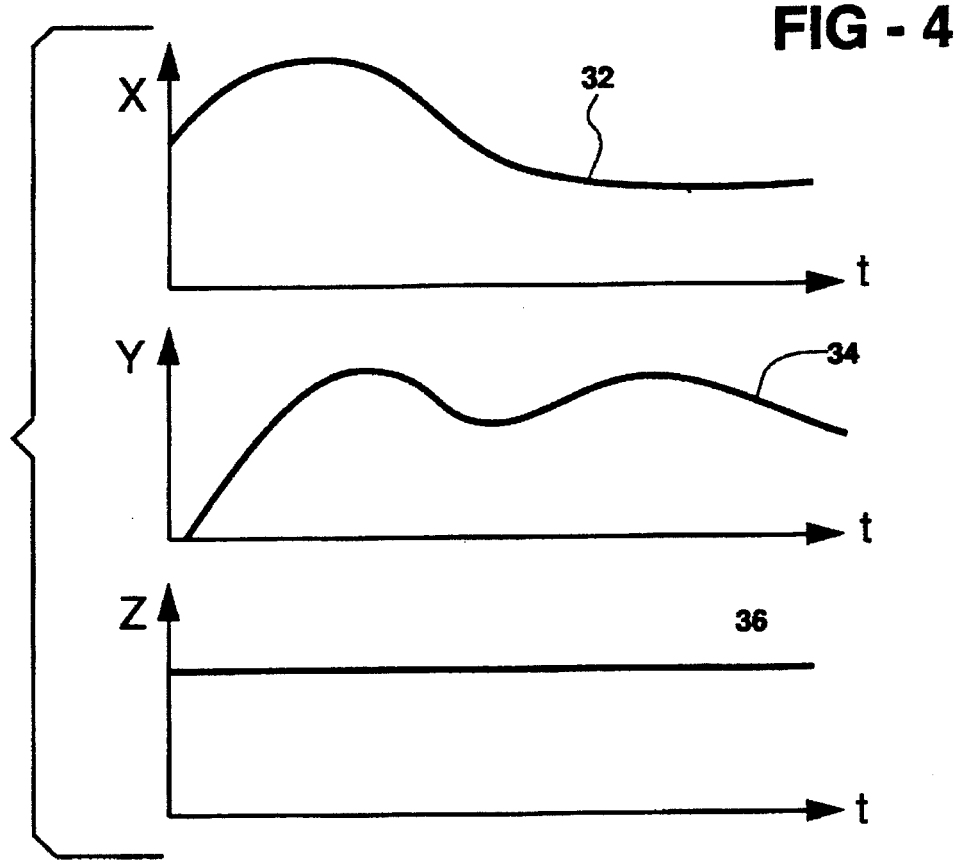
FIG. 4 is a graphic representation of each of the components of the single highlight line of FIG. 3.
Figure 5:
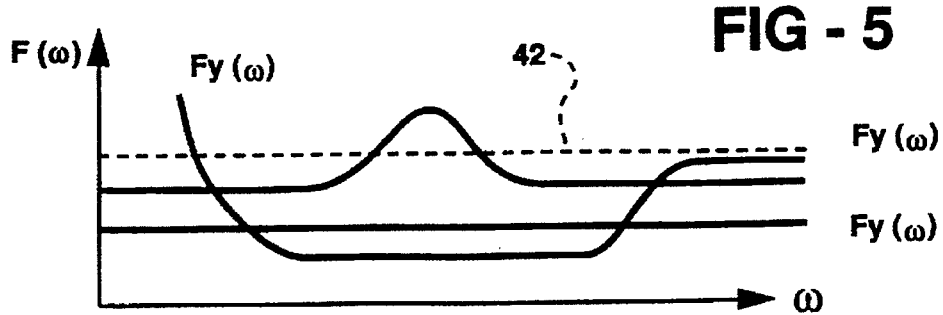
FIG. 5 is a graphic representation of the frequencies associated with the spatial information of FIG. 4.

The highlight lines 18 are individually decomposed into their x-, y-, and z- coordinates or components 32, 34, 36, at 38. An individual highlight line 18 as depicted in FIG. 3 is decomposed into its individual spatial elements as depicted in FIG. 4. Upon decomposition, the spatial data is transformed into frequency data at 40. The frequency components are shown in FIG. 5 and are shown for example only. In one embodiment, the transform used is a Fourier transform. It should be appreciated by those skilled in the art that any other transform function may be appropriately used. Once transformed, the frequency data is compared with a threshold frequency signal 42 at 44. If any of the frequency data $F_x(\omega)$, $F_y(\omega)$ or $F_z(\omega)$ should exceed the threshold frequency signal 42 at 46, the frequency is identified at 48. The threshold frequency signal 42 is the objective test to determine if a portion of the smooth surface 12 is flawed. By using the threshold frequency signal 42, it does not matter if the flaw 10 is a protrusion or a recession in the smooth surface 12 because the threshold frequency signal 42 is used to measure changes in frequency and not the direction of the slope of the flaw 12. If not, the smooth surface 12 is identified as satisfactory at 50 and a production model for tool fabrication is manufactured at 52. Surfaces are added to the model to be manufactured at 54 for tooling purposes. Another prototype is created at 56 which is tested again. If any failed locations are detected, it is determined whether any of the locations are statistically significant at 58. If the failed locations are not, the model is refined at 60 and retested at 58. If the failed location is significant, i.e., if the removal of the flaw alters the prototype tool surface, the design is returned to a preliminary design step at 62 and a new prototype of the smooth surface 12 is created. It should be appreciated that the detection of flaws 10 at block 58 is accomplished by going through steps similar to steps 26 through 50, a discussion of which is found above and not repeated at this time.

Returning to decision block 46, if the frequency data has exceeded the threshold frequency signal 42, the frequency is identified or tagged at 48. The frequency data for the smooth surface 12 is inversely transformed back into the spatial data at 64 where the tagged data identifies the failed location at 66. Upon identifying the failed location, the model is refined at 62 for an eventual redesign at 22.

If, at 58, no failed locations are identified, the tool prototype surface model is released for the creation of the production-ready master model at 68, from which tools used to create objects having the smooth surface 12 are fabricated therefrom.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced otherwise than as specifically described.

What is claimed is:

1. A method for locating flaws in a smooth surface using at least one light source, the method comprising the steps of:

setting the light source a predetermined length above the smooth surface;

locating a highlight line;

translating the light source across the smooth surface to create a plurality of highlight lines;

decomposing each of the highlight lines into their respective spatial components;

measuring spatial parameters of each of the highlight lines;

transforming the spatial parameters into frequency parameters;

comparing the frequency parameters to a threshold;

identifying frequency parameters exceeding the threshold signal; and locating flaws in the smooth surface.

2. A method as set forth in claim 1 including the step of inversely transforming the frequency parameters into spatial parameters to locate the flaws.

3. A method as set forth in claim 2 including the step of locating the spatial parameters associated with the frequency parameters exceeding the threshold signal to locate the flaws in the smooth surface.

4. A method for locating flaws into a smooth surface using a plurality of light sources, the method comprising the steps of:

setting the light sources at a predetermined length above the smooth surface;

locating highlight lines, each of the highlight lines created by each of the light sources;

decomposing each of the highlight lines into their respective spatial components;

measuring spatial parameters of each of the highlight lines;

transforming the spatial parameters into frequency parameters;

comparing the frequency parameters to a threshold;

identifying frequency parameters exceeding the threshold signal; and locating flaws in the smooth surface.

5. A method for fabricating an object having a smooth surface using at least one light source, the method comprising the steps of:

defining a preliminary piece source a predetermined length above the smooth surface;

locating a highlight line;

translating the light source across the smooth surface to create a plurality of highlight lines; locating flaws in the smooth surface;

illuminating the flaws from the smooth surface of the preliminary piece;

shaping a tool to produce the piece from the preliminary piece after eliminating the flaws therefrom;

setting the light source a predetermined length above the tool;

locating a highlight line;

translating the light source across the tool to create a plurality of highlight lines;

decomposing each of the highlight lines into their respective spatial components;

measuring spatial parameters of each of the highlight lines;

transforming the spatial parameters into frequency parameters;

comparing the frequency parameters to a threshold;

identifying frequency parameters exceeding the threshold signal; and locating flaws in the tool.

6. A method as set forth in claim 5 including the step of redefining the preliminary piece when removing the flaws from the tool alters the smooth surface of the tool.

7. A method as set forth in claim 5 including the step of forming the piece from the tool.

* * * * *